(12) United States Patent
Zavislan et al.

(10) Patent No.: US 8,115,918 B2
(45) Date of Patent: *Feb. 14, 2012

(54) IMAGING OF SURGICAL BIOPSIES

(75) Inventors: James M. Zavislan, Pittsford, NY (US); Roger J. Greenwald, San Diego, CA (US)

(73) Assignee: Lucid, Inc., Rochester, NY (US)

( * ) Notice: Subject to any disclaimer, the term of this patent is extended or adjusted under 35 U.S.C. 154(b) by 1294 days.

This patent is subject to a terminal disclaimer.

(21) Appl. No.: 11/788,920

(22) Filed: Apr. 23, 2007

(65) Prior Publication Data

US 2007/0195308 A1 Aug. 23, 2007

Related U.S. Application Data

(63) Continuation of application No. 09/786,901, filed on Mar. 9, 2001, now Pat. No. 7,227,630.

(60) Provisional application No. 60/100,179, filed on Sep. 14, 1998.

(51) Int. Cl.
*G01N 21/01* (2006.01)

(52) U.S. Cl. .................................................. 356/244

(58) Field of Classification Search ............... 422/99; 356/244

See application file for complete search history.

(56) References Cited

U.S. PATENT DOCUMENTS

| 3,480,504 A | 11/1969 | Good et al. |
| 3,556,633 A | 1/1971 | Mutschmann et al. |
| 4,415,107 A | 11/1983 | Palmieri |
| 4,974,952 A | 12/1990 | Focht |
| 5,002,735 A * | 3/1991 | Alberhasky et al. ............ 422/99 |
| 5,034,613 A | 7/1991 | Denk et al. |
| 5,073,857 A | 12/1991 | Peters et al. |
| 5,076,680 A | 12/1991 | Arjarasumpun |
| 5,103,338 A | 4/1992 | Crowley et al. |
| 5,156,150 A | 10/1992 | Lary |
| 5,271,414 A | 12/1993 | Partika et al. |

(Continued)

FOREIGN PATENT DOCUMENTS

DE 33 23 742 A1 1/1985

(Continued)

OTHER PUBLICATIONS

Corcuff, P. et al., Morphometry of Human Epidermis in vivo by Real-time Confocal Microscopy, Arch Dermatol Res, 265, pp. 475-481, 1993.

(Continued)

*Primary Examiner* — Jamara Franklin
(74) *Attorney, Agent, or Firm* — Kenneth J. Lukacher

(57) ABSTRACT

Encapsulated tissue is contained in an optically transparent cassette (34). The cassette (34) or an endcap (38) enclosing the cassette is marked with a fiducial (40) indicating and corresponding to the location of the excision on the patient's body. An image, which is preferably a representation of a surface of the tissue specimen and the vertical section(s) area of the tissue internal of the specimen and adjacent to a surface thereof, is obtained by an imaging system (10). The cassette is moved, preferably in a stage (22) which rotates the cassette while translating it, so that the head (12) of the imaging system provides a linear scan in a direction perpendicular to the wall of the cassette (also perpendicular to the surface of the tissue encapsulated in the cassette). The imaging system's display (28) indicates the morphology at and in proximity to the surface of the specimen as well as the location thereof.

15 Claims, 2 Drawing Sheets

U.S. PATENT DOCUMENTS

Figure 1:
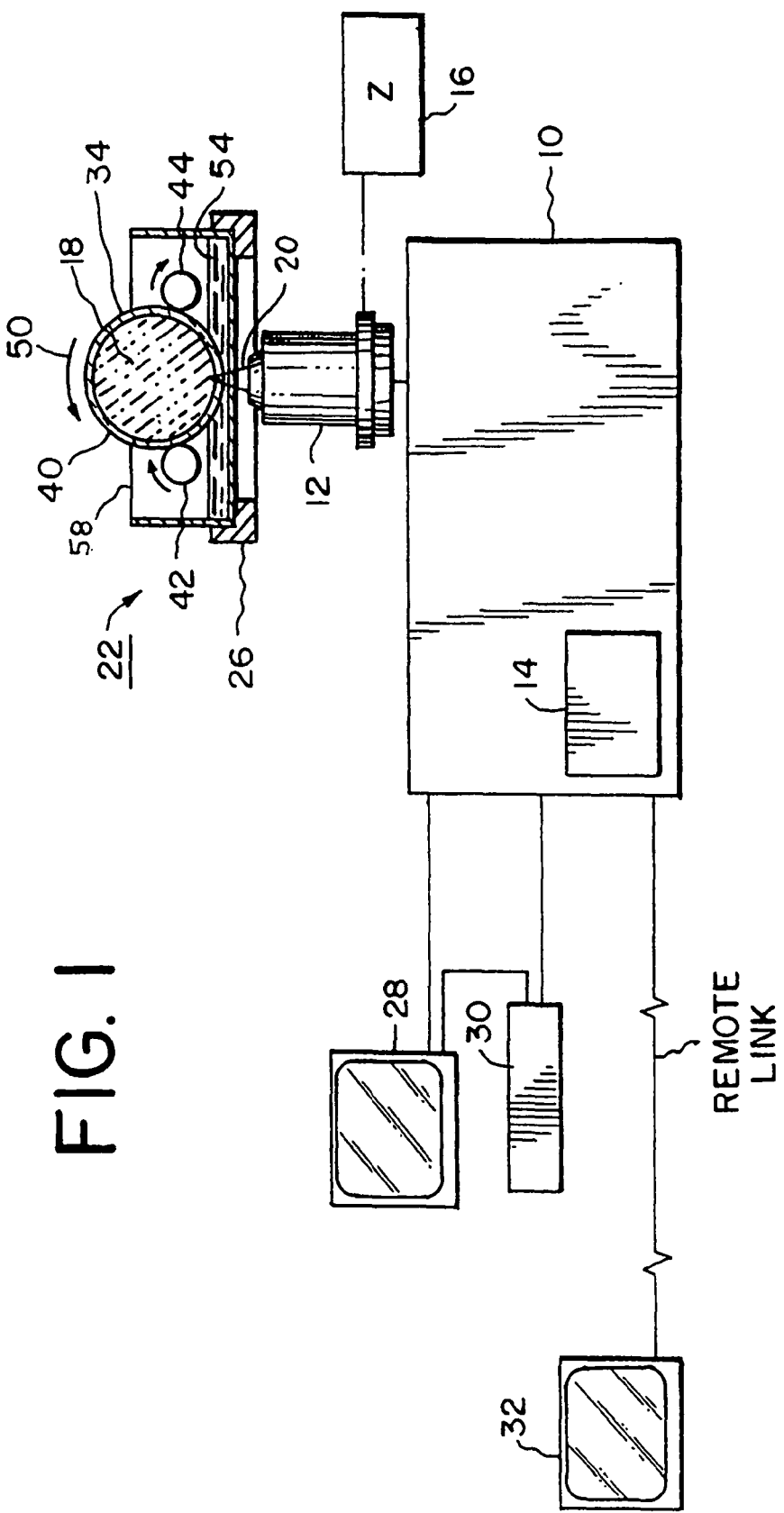

| | | | |
|---|---|---|---|
| 5,383,234 A | 1/1995 | Russell | |
| 5,383,472 A | 1/1995 | Devlin et al. | |
| 5,554,151 A | 9/1996 | Hinchliffe | |
| 5,609,827 A | 3/1997 | Russell et al. | |
| 5,649,547 A | 7/1997 | Ritchart et al. | |
| 5,719,700 A | 2/1998 | Corcuff et al. | |
| 5,788,639 A | 8/1998 | Zavislan et al. | |
| 5,832,931 A * | 11/1998 | Wachter et al. | 128/898 |
| 5,836,877 A | 11/1998 | Zavislan | |
| 5,870,223 A | 2/1999 | Tomimatsu | |
| 5,880,880 A | 3/1999 | Anderson et al. | |
| 5,978,695 A | 11/1999 | Greenwald et al. | |
| 5,995,867 A | 11/1999 | Zavislan et al. | |
| 6,014,451 A | 1/2000 | Berry et al. | |
| 6,032,071 A | 2/2000 | Binder | |
| 6,151,127 A | 11/2000 | Kempe | |
| 6,330,106 B1 | 12/2001 | Greenwald et al. | |
| 6,411,434 B1 | 6/2002 | Eastman et al. | |

FOREIGN PATENT DOCUMENTS

| | | |
|---|---|---|
| EP | 0821256 | 1/1998 |
| WO | WO 96/21938 | 7/1996 |
| WO | 99/08588 | 2/1999 |
| WO | WO 00/49392 | 8/2000 |
| WO | WO 00/49447 | 8/2000 |

OTHER PUBLICATIONS

Rajadhyaksha, M. et al., Confocal Laser Microscope Images Tissue in vivo, Laser Focus World, pp. 1-4, Feb. 1997.

Rajadhyaksha, M. et al., In Vivo Confocal Scanning Laser Microscopy of Human Skin: Melanin Provides Strong Contrast, The Journal of Investigative Dermatology, vol. 104, No. 6, pp. 946-952, 1995.

Schmidt, W. et al., Principles and Techniques of Surgical Pathology, Addison-Wesley Publishing Company, pp. 367-368, 1983.

Schmitt, J. et al., Optical Characterization of Dense Tissues Using Low-Coherence Interferometry, SPIE, vol. 1889, pp. 197-211, 1993.

* cited by examiner

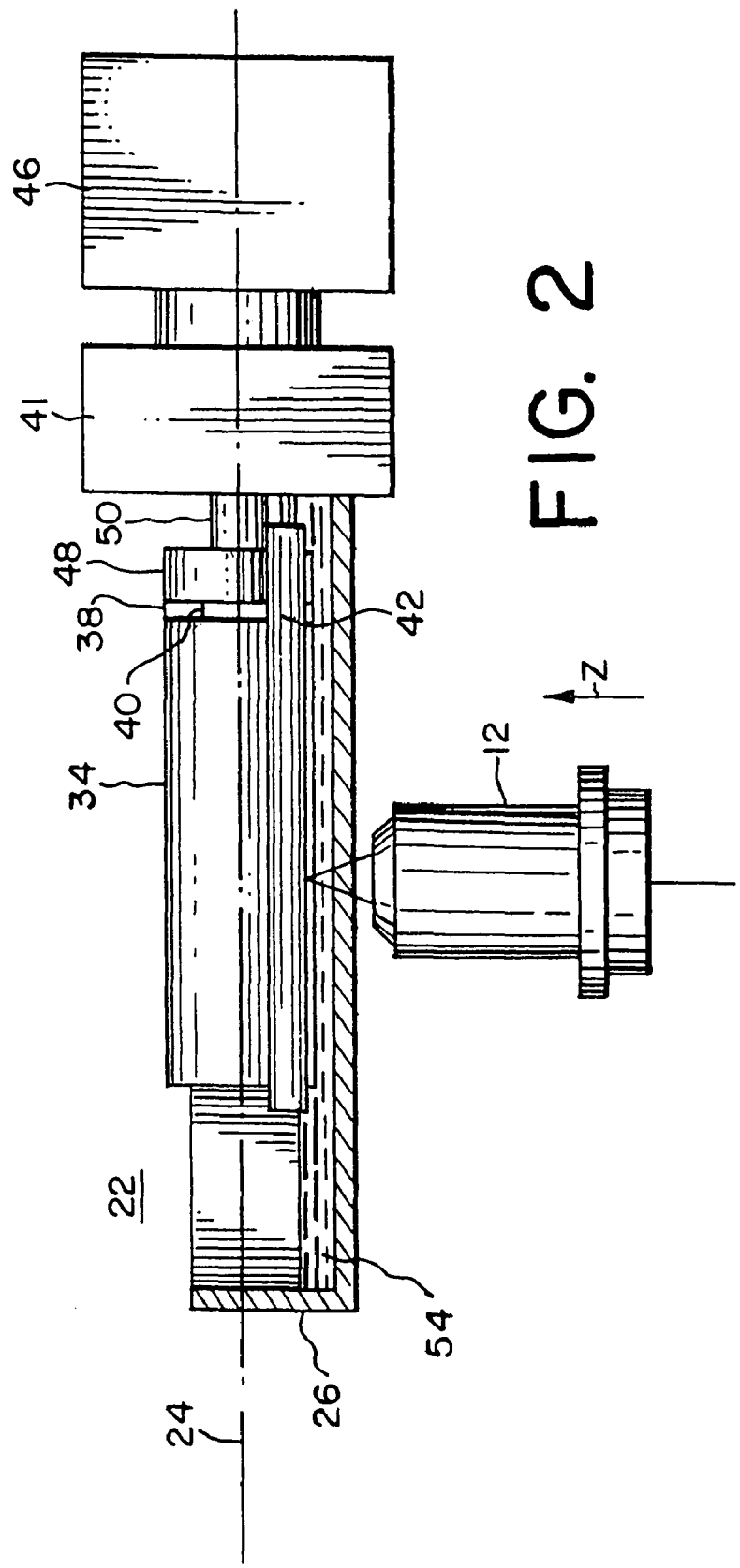

IMAGING OF SURGICAL BIOPSIES

This application is a continuation of U.S. patent application Ser. No. 09/786,901, filed 9 Mar. 2001, now U.S. Pat. No. 7,227,630, which claims the priority benefit of U.S. Provisional Application No. 60/100,179, filed 14 Sep. 1998.

DESCRIPTION

The present invention relates to imaging of biopsies (tissue specimens) and particularly to systems (methods and apparatus) for providing images of surgically removed tissue material from which images suitable for pathological examination, without delay for tissue preparation, such as freezing, sectioning, staining and mounting on microscope slides.

Confocal laser scanning microscopes, such as the Vivascope® sold by Lucid, Inc. of Henrietta, N.Y., US and described in the Journal of Investigative Dermatology, Volume 104 No. 6, June, 1995, pp. 1-7 and International Patent Publication, WO-96/21938, published Jul. 18, 1996, and in U.S. Pat. No. 5,788,639, issued Aug. 4, 1998 provide images of tissue sections on a patient which may be taken in vivo, without biopsy procedures taken. Pathological examination of these images can reveal the morphology of the tissue in a body region of interest rapidly and without the need for tissue preparation as conventionally used by pathologists. In many cases, such as in case of breast cancer examinations and treatment, tissue is excised, which is deeply disposed within the patient's body. Incisional or excisional biopsies may be taken by standard surgical methods—small needle core or large gauge cannular core. Incisions and excisions which are used for biopsies, either as biopsy samples or as excisional biopsies, which are intended to completely remove the abnormality, nevertheless must be examined so that the surgeon and pathologist can determine whether the biopsy sample has been taken in the location of the tissue of interest and whether the excisional biopsy has completely removed the abnormality. In such cases, pathological examination has delayed and extended the time for the surgical procedure to provide the biopsies. This is because of the time needed for preparation of tissue sections from biopsies to the pathologist for examination under a microscope. Such preparation procedures include freezing, sectioning, staining and mounting on microscope slides.

The present invention enables the use of laser scanning confocal microscopy, such as described in the documents referenced above and other rapid electro-optical imaging techniques, such as optical coherence tomography (see, Optical characterization of disease tissue using low coherence interferometry, Proceedings of SPIE, Volume 1889 (1993)) and two photon laser microscopy (see, for example U.S. Pat. No. 5,034,613 to Denk, et al., issued Jul. 23, 1991), to be used to provide images of excised tissue, particularly biopsies. The electronic images produced by these imaging systems may be used by the pathologist to determine whether the biopsy has been successfully performed and the excision has been made in the proper location without the delay incidental to tissue preparation.

Briefly described, the invention may be carried out by encapsulating the tissue specimen, preferably during the excision procedure in an optically transparent carrier, such as a cassette, the walls of which confine the specimen under tension or compression. For the case of breast biopsies, the cassette is preferably made of a radiographic transparent material to allow for radiographic examination of breast biopsies. Radiographic examination verifies suspect breast tissue is inside the cassette. The cassette is then moved, preferably translated and rotated in azimuth about an axis through the cassette, while being scanned by an imaging system. The imaging system provides an electronic display of the surface of the tissue sample, as well as the volume adjacent to the surface. In addition, a mark or fiducial on the cassette indicates and corresponds to a position of the excision such that the image displayed contains information as to the location of the excisioned tissue material in the patient's body. No tissue preparation is necessary and the pathologist can determine from the display whether the excision is in the proper location as in the case of excisional biopsies, or has removed the abnormal material (e.g., the breast cancer nodule) entirely without leaving any apparently abnormal tissue in place.

The present invention has as its principal feature therefore, providing an improved system for the handling and imaging of biopsy samples which enable the use of electro-optical imaging techniques and to benefit from the facilities such techniques which provide for rapid and convenient pathological examination of biological tissue.

The foregoing and other features, objects and advantages of the invention will become more apparent from a reading of the following description in connection with the accompanying drawings in which:

FIG. 1 is a schematic and block diagram of a system which enables electro-optical imaging of excised tissue samples, such as biopsies and the like with a confocal laser scanning microscope (CLSM); and FIG. 2 is another schematic view illustrating the stage which manipulates an encapsulated sample in accordance with the invention.

Referring to the drawings, there is shown a confocal imaging system 10 which includes a head, in the case of a CLSM, containing an objective lens and is referred to as the objective lens 12. Associated with the confocal imaging system is a control system 14. This control system controls actuators associated with the objective lens 12, particularly an actuator 16 which moves the objective lens along a z axis, that is towards and away from the tissue specimen 18 and particularly the surface of the specimen 18, such that the focus of the confocal beam 20 can be advanced into and out of the specimen. In addition, the control system can control the motors and other actuation mechanism of a stage 22 by which the specimen 18 is manipulated. This manipulation includes the rotation about a longitudinal axis 24 (FIG. 2) and translation in a direction along the axis 24 by an axial motion mechanism 26.

Also associated with the confocal imaging system 10 is a display 28 on which an image of the specimen is obtained. The images can take the form of spiral projections of the tissue at a given depth at or below the tissue surface. This image can be produced by continuously translating the tissue cassette along axis 24 as the cassette rotates. The translation carries the cassette approximately one field of view for each complete revolution of the cassette. In this mode, the width of the image is set, by the field of view (FOV) of the confocal scan optics, at the focus of objective 12. The length of the image is 2Π r L/FOV, where r is the cassette radius, L is the length of the biopsy, and FOV is the transverse field of view. The second image representation is a vertical projection in which the objective lens 12 is scanned from the tissue surface into the tissue at a given rotational position and longitudinal position along axis 24. In this representation, the width of the image is the FOV and the height of the image is set by the scan depth. This image represents a vertical cross section of tissue morphology.

Numerous vertical sections can be taken around the perimeter of the tissue to sample the biopsy surface. This image representation is analogous to standard vertical section pathologic preparation and examination.

Furthermore, a combination of imaging representations can be used. For example, portions of the tissue are surveyed with abbreviated or continuous spiral scans. Vertical sections can be scanned at various locations. The vertical section images can be combined with spiral projections to better represent the morphology of the tissue biopsy. The image can map a sheet which extends substantially perpendicular to the external surface of the specimen, thus constituting a volumetric representation of the surface of the specimen 18 and the tissue adjacent thereto. This image therefore is useful in showing the morphology of the biopsy (excision or incision) to the pathologist and may direct further surgical procedures (biopsies) and indicate whether such further procedures are necessary.

The image to be displayed may be stored in a memory or image storage which may be disc or solid state memory 30 which obtains the information from the imaging system 10 and presents it for display on the image display 28.

The images need not be displayed on site where the imaging system 10 and the stage 22 are located, but may be connected by a remote link, such as a wire radio or fiber optic link, to a remote image display 32. Such remote imaging for examination of tissue is the subject matter of Zavislan et al., U.S. Pat. No. 5,836,877, issued 11 Nov. 1998.

The invention provides for the encapsulation of the tissue specimen 18 in a cassette (or canister) 34. This cassette is made of transparent material. A preferable cassette material is amorphous polyoelefin, which is preferred because of its low birefringence. Such material is sold under the tradename Zeonex by the BF Goodrich Company of Akron, Ohio, US and is manufactured by Nippon Zeon Company, Ltd., their grade E-48R being suitable.

The cassette 34 is generally cylindrical and is closed at the ends by endcaps, one of which 38, is shown in FIG. 2. This endcap or the cassette itself has a mark or position fiducial 40 which may be a groove in the cap. This groove is aligned with an indicia on the incision site to provide a reference location on the image which is displayed so that the pathologist can relate the location of the image to the location of the excision on the patient's body. The fiducial may be scanned by the confocal imaging system. Alternatively, the fiducial 40 is referenced to an encoder 46 (FIG. 2) oriented with respect to the axial or azimuth drive which rotates the cassette 34. This rotation may be obtained by a motor 41 which drives directly or through a gear system to drive and support rollers 42 and 44. The encoder 46 has a reference mark which may be aligned in an exact/or correlated azimuth relationship with the fiducial. The position information is provided by the encoder to the control system 14 and also to the display 28, as well as being contained in storage 30. The display therefore provides position information referenced to the fiducial on the cassette 34 or cap 38 which is in turn referenced to the excision. For example, the excision may be attached to a removable ring which is adhesively connected to the skin. The ring may be marked with an indicium or fiducial which indicates a reference point on the excision. Indicium is indexed and aligned with the fiducial on the cassette 34 or cap 38 thereby providing the positional information either from the scanning of the cassette or by means of the encoder 46.

The alignment of the encoder 46 with the cassette 34 may be carried out by means of a flange 48 attached to and rotatable with the motor shaft 50. The flange may be rotated with respect to the cassette 34 and cap 38 about the axis 24 and then attached to the cap by suitable fasteners which provide a sufficient mechanical coupling between the motor and the cassette. The encoder is thereby aligned by aligning its reference mark (usually on the surface of the encoder) with the reference mark or fiducial 40 on the cassette 34 or cap 38.

The rotational drive for the cassette 34 may be by means of the drive and support rollers 42 and 44, which rotate in the same direction, as indicated in FIG. 1 by the arrows adjacent thereto. This provides for rotation of the cassette in direction of the arrow 50 as shown in FIG. 1. While the cassette is rotating, the axial motion mechanism 26, which may include a lead screw mechanism, provides for movement along the axis such that the scan follows a corkscrew or helical path. The image is made by reflections from the focus of the confocal beam. This focus may oscillate inwardly and outwardly so as to trace a sheet which represents about 80% of the volume at and adjacent to the surface of the specimen 34. Alternatively, instead of an axial motion mechanism 26, the guide rollers may have a helical or screw-type surface so that the rotation thereof will provide axial motion of the specimen cassette 34. Various other means for axial and rotational motion to provide a helical scanning path may also be adapted for use in the stage 22.

In order to provide for matching of the index of refraction of the tissue sample, an index matching liquid 54 may be used in a container or tank 58 of the stage 22. The index of the cassette 34 may match the index of the tissue material in the cassette. In addition, the index of the liquid 54 may match the index of the material of the cassette. The index matching fluid may for example be a water solution which has an index of approximately 1.33. The slight difference in the index of the tissue and the cassette which provides for optical aberration (for example, astigmatism because of the cylindrical geometry), may be corrected, if found objectionable by the pathologist, by means of a correction lens in the objective lens unit 12 or by changing the refractive index of the matching liquid 54.

A tissue preservation fluid such as saline or other suitable tissue preservative fluid is inside the cassette 34 with the tissue 18 to ensure that no air bubbles are between the tissue and the cassette's inner surface.

The tissue specimen is excised and encapsulated in the cassette 34, preferably as part of the excision or biopsy procedure as carried out by the surgeon. In order to provide the transparent cassette 34, the trocar which is used to make the excision may provide the cassette 34. Alternatively, a conventional instrument for making the excision, such as shown in Ratcliff, U.S. Pat. No. 5,709,697, issued Jan. 20, 1998, may be used. The excision is held under tension by a corkscrew member of the instrument and may be deposited into the cassette and removed. The cassette may be part of a cannula through which the excision instrument is inserted. The cassette may be the outer part of the cannula and may be connected thereto as by a bayonet quick release connection. The cassette is the same size or slightly smaller than the excised tissue specimen and is held in the cassette. The endcaps are placed on the cassette after excision. The cassette may be closed at one end and capped at the other. In order to keep the tissue moist, a sponge/gauge pad, impregnated with saline or other suitable tissue preservative fluid, may be contained in the cassette, preferably at an end thereof and held in place by the cap.

Modifications and variations in the herein described method and system will undoubtedly suggest themselves to those skilled in the art. Accordingly, the foregoing description should be taken as illustrative and not in a limiting sense.

The invention claimed is:

1. A system for imaging biopsy tissue which comprises means for encapsulating an excised tissue specimen in compression in a transparent holder, and means for scanning said holder and providing at least one image representing an optically formed section of the tissue specimen suitable for pathological examination.

2. The system as set forth in claim 1 further comprising means for providing alignment of said specimen with an indicia or fiducial mark on said holder, and means for referencing said image with respect to said mark.

3. The system as set forth in claim 2 further comprising an encoder coupled to said holder for providing signals correlated positionally with said scanning means.

4. The system according to claim 1 wherein said holder is cylindrical.

5. A system for imaging a tissue sample comprising:
   means for encapsulating the tissue sample in a cassette;
   means for scanning the cassette to provide at least one image representing an optically formed section of the tissue sample suitable for pathological examination.

6. The system according to claim 5 wherein said cassette is of a material optically transparent to said scanning system.

7. An apparatus for imaging of surgical biopsies which comprises an instrument for making an incision or excision in tissue of a body to provide a tissue specimen, a transparent cassette for encapsulating said specimen under compression, and an imaging system for scanning said cassette to provide at least one image representing an optically formed section of the excised tissue specimen suitable for pathological examination of said specimen.

8. An apparatus for imaging an excised tissue specimen without histological preparation of at least sectioning, staining, and mounting on slides, said apparatus comprising:

a holder for the non-histologically prepared tissue specimen in which the tissue specimen is held in compression in said holder; and an imager for imaging the tissue specimen in said holder to provide at least one image representing an optically formed section of the excised tissue specimen suitable for pathological examination.

9. The apparatus according to claim 8 wherein said imager comprises an objective lens, and said objective lens and said holder are movable with respect to each other to image sections at various locations of said tissue specimen.

10. The apparatus according to claim 8 wherein said imager is capable of representing an optically formed section at a depth below the surface of said tissue specimen.

11. The apparatus according to claim 8 wherein said imager is operative in accordance with optical coherence tomography.

12. The apparatus according to claim 8 wherein said imager is operative in accordance with two-photon microscopy.

13. The apparatus according to claim 8 wherein said imager is a confocal imaging system.

14. The apparatus according to claim 8 wherein the tissue specimen is imagible by said imager through a part of said holder which is optically transparent to said imager.

15. The apparatus according to claim 8 wherein said holder is cylindrical.

* * * * *